(12) United States Patent
Brahmbhatt et al.

(10) Patent No.: US 8,043,557 B2
(45) Date of Patent: Oct. 25, 2011

(54) METHODS AND SYSTEMS FOR SANITIZING OR STERILIZING A MEDICAL DEVICE USING ULTRASONIC ENERGY AND LIQUID NITROGEN

(75) Inventors: Sudhir R. Brahmbhatt, Glencoe, MO (US); Richard R. Masi, Perkiomenville, PA (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 11/839,100

(22) Filed: Aug. 15, 2007

(65) Prior Publication Data
US 2009/0047175 A1 Feb. 19, 2009

(51) Int. Cl.
| A61L 2/00 | (2006.01) |
| A61L 2/04 | (2006.01) |
| A61L 2/18 | (2006.01) |
| A61L 9/00 | (2006.01) |
| A61L 11/00 | (2006.01) |

(52) U.S. Cl. ............... 422/20; 422/1; 422/28; 422/292
(58) Field of Classification Search ............ 422/20, 422/128, 28, 1, 292
See application file for complete search history.

(56) References Cited

U.S. PATENT DOCUMENTS

| 3,007,478 A * | 11/1961 | Leonhardt et al. ......... 134/57 R |
| 3,934,379 A | 1/1976 | Braton et al. |
| 4,596,133 A | 6/1986 | Smalling et al. |
| 5,213,619 A * | 5/1993 | Jackson et al. ............ 134/1 |
| 5,258,413 A | 11/1993 | Isayev |
| 5,284,625 A | 2/1994 | Isayev et al. |
| 5,316,591 A | 5/1994 | Chao et al. |
| 5,456,759 A | 10/1995 | Stanford, Jr. et al. |
| 5,927,302 A | 7/1999 | Hayami et al. |
| 5,943,869 A * | 8/1999 | Cheng et al. ............. 62/121 |
| 6,030,344 A | 2/2000 | Guracar et al. |
| 6,086,539 A | 7/2000 | Guracar et al. |
| 6,093,149 A | 7/2000 | Guracar et al. |
| 6,110,118 A | 8/2000 | Guracar et al. |
| 6,193,664 B1 | 2/2001 | Guracar et al. |
| 6,241,677 B1 | 6/2001 | Guracar et al. |
| 6,258,029 B1 | 7/2001 | Guracar et al. |
| 6,322,511 B1 | 11/2001 | Guracar et al. |
| 6,343,609 B1 | 2/2002 | Kim |
| 6,447,718 B1 * | 9/2002 | Carter et al. ............ 422/20 |
| 6,464,640 B1 | 10/2002 | Guracar et al. |
| 6,482,584 B1 * | 11/2002 | Mills et al. ............ 435/1.1 |
| 6,733,727 B1 * | 5/2004 | Kullberg ............... 422/20 |

(Continued)

FOREIGN PATENT DOCUMENTS

JP 02257613 A * 10/1990

(Continued)

OTHER PUBLICATIONS

IBM, Subcooler for Liquid Nitrogen Cooling of Electronic Circuits With Direct Vapor Cycle refrigeration, Jun. 1990, IB Technical Disclosure Bulletin, NA9008279.

(Continued)

*Primary Examiner* — Sean E Conley
*Assistant Examiner* — Regina Yoo
(74) *Attorney, Agent, or Firm* — Allen E. White

(57) ABSTRACT

A medical device is sterilized or sanitized by at least partially submerging it within liquid nitrogen and imparting ultrasonic energy to it.

14 Claims, 5 Drawing Sheets

U.S. PATENT DOCUMENTS

| | | | |
|---|---|---|---|
| 6,912,858 B2 * | 7/2005 | White | 62/50.5 |
| 2004/0134794 A1 | 7/2004 | Sundaram et al. | |
| 2004/0181236 A1 * | 9/2004 | Eidenschink et al. | 606/108 |
| 2005/0097900 A1 * | 5/2005 | Giacobbe et al. | 62/64 |
| 2005/0172984 A1 | 8/2005 | Schweitzer et al. | |
| 2007/0154347 A1 | 7/2007 | Novak et al. | |
| 2007/0260109 A1 * | 11/2007 | Squillace | 600/36 |
| 2009/0044828 A1 | 2/2009 | Brahmbhatt et al. | |

FOREIGN PATENT DOCUMENTS

| | | | |
|---|---|---|---|
| JP | 03190131 A | * | 8/1991 |
| JP | 05-13393 A | * | 1/1993 |

OTHER PUBLICATIONS

Office Action dated Dec. 22, 2010 for U.S. Appl. No. 11/839,153.

* cited by examiner

# METHODS AND SYSTEMS FOR SANITIZING OR STERILIZING A MEDICAL DEVICE USING ULTRASONIC ENERGY AND LIQUID NITROGEN

CROSS-REFERENCE TO RELATED APPLICATIONS

This application is related to U.S. patent application Ser. No. 11/839,153, filed concurrently herewith entitled, "METHODS AND SYSTEMS FOR DEBONDING AN UNDESIRABLE MATERIAL FROM A DEVICE USING ULTRASONIC ENERGY AND LIQUID NITROGEN.

BACKGROUND

The selection of the proper method for the sanitization and deep cleaning of medical devices, such as surgical instruments, is always a concern. This is because many of those methods are not simple or economical.

Surgical instruments constitute a significant portion of hospital cleaning, decontamination and sterilizing requirements. The complexity of instrument design and nature of surgical soil compound the problems of surgical instrument processing. Surgical instruments usually have multiple joints, hinges, crevices, grooves, holes, cracks, or serrated edges which may harbor large amounts of soil. The soil itself is usually composed of protein or other organic material which often has been fixed in place by heat or chemicals. Furthermore, the necessity for decontamination of soiled instruments with a minimum of risk to the staff adds to the complexity of the problem.

Commercially available apparatus for preparing surgical instruments for reuse has required multiple handling steps and separate pieces of equipment. An example of a standard method of processing surgical instruments calls for placements of the instruments in a washer/sterilizer which has a cleaning phase which removes the gross soil and decontaminates the instruments with high temperature steam (normally 270° F.). Since soil which is not removed tends to be fixed in place by the steam, the instruments are then transferred to a sonic cleaner. Following sonic cleaning the instruments are terminally sterilized. This technique requires multiple handling of instruments and multiple pieces of equipment.

Sterilants are used in many areas, such as in the sterilization of laboratory, surgical, dental and other equipment. Since these chemical sterilizing agents or other chemical sterilizing methods commonly take six to ten (6-10) hours to be effective, it is customary in hospital practice to chemically sterilize instruments overnight.

Methods of sterilization involving either the use of pressurized steam, dry heat or ethylene oxide are common. However, some of these methods are cumbersome, tedious and time-consuming employing potential carcinogens often damage the sterilized material and require expensive equipment and skilled technicians. Moreover, steam or heat sterilization is impracticable for many plastic devices and delicate instruments which are sensitive to elevated temperatures.

SUMMARY

There is disclosed a method of disinfecting or sterilizing medical devices, including the following the steps. A vessel containing liquid nitrogen is provided. A medical device having microorganisms on a surface thereof is provided. At least a portion of the surface is immersed in the liquid nitrogen within the vessel. Ultrasonic wave energy is caused to be applied to the medical device.

There is also disclosed a method of sterilizing or sanitizing a medical device that includes submerging the medical device within liquid nitrogen and imparting ultrasonic energy to the medical device while submerged.

There is also disclosed a system for disinfecting or sterilizing medical devices, including: a container containing liquid nitrogen; a medical device holding member operably associated with the container; a medical device held by the medical device hanging member, wherein the medical device has a surface to be a cleaned; and a sonicating member at least partially extending into the liquid nitrogen and being adapted and configured to impart ultrasonic waves to the surface.

The method and/or system can include one or more of the following aspects:
- the device is a stainless steel surgical instrument, and performance of said step of applying results in destruction of at least some of the microorganism.
- the device is a syringe, and performance of said step of applying results in destruction of at least some of the microorganism.
- said step of providing a vessel containing liquid nitrogen comprises the steps of passing high pressure liquid nitrogen through a subcooler where it is subcooled and allowing the subcooled liquid nitrogen to flow into the vessel.
- the ultrasonic waves have a frequency of greater than 20 kHz to about 50 kHz.
- the ultrasonic waves have a frequency of about 50 kHz to about 100 kHz.
- the liquid nitrogen is subcooled and has a temperature in a range of from about −196° C. to about −173° C.
- the liquid nitrogen is subcooled and has a pressure in a range of from about 4 bar to about 14 bar.
- the medical device comprises a surgical instrument.
- the medical device comprises a curette.
- the medical device comprises a dental instrument.
- the medical device comprises a medical implant.
- the medical device comprises a dental implant.
- a source of liquid nitrogen and a cooling member are included, wherein:
  - wherein the source and cooling member are in fluid communication with each other
  - said cooling element has an inlet adapted and configured to receive liquid nitrogen from said source of liquid nitrogen, a coil portion in fluid communication with said inlet and submerged within said liquid nitrogen contained within said container, and an outlet in fluid communication with said coil and being adapted and configured to vent nitrogen from said cooling element.
- a lid member is included, wherein the lid member extends over, and is sized to cover, a top end of said container, and said lid member has a vent adapted and configured to vent gaseous nitrogen from a headspace in said container above said liquid nitrogen.
- the liquid nitrogen is open to the atmosphere.
- the medical device is totally immersed within the liquid nitrogen.
- a degree of sanitization or sterilization of the microorganism is determined after performance of said steps of providing, immersing, and causing are performed.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
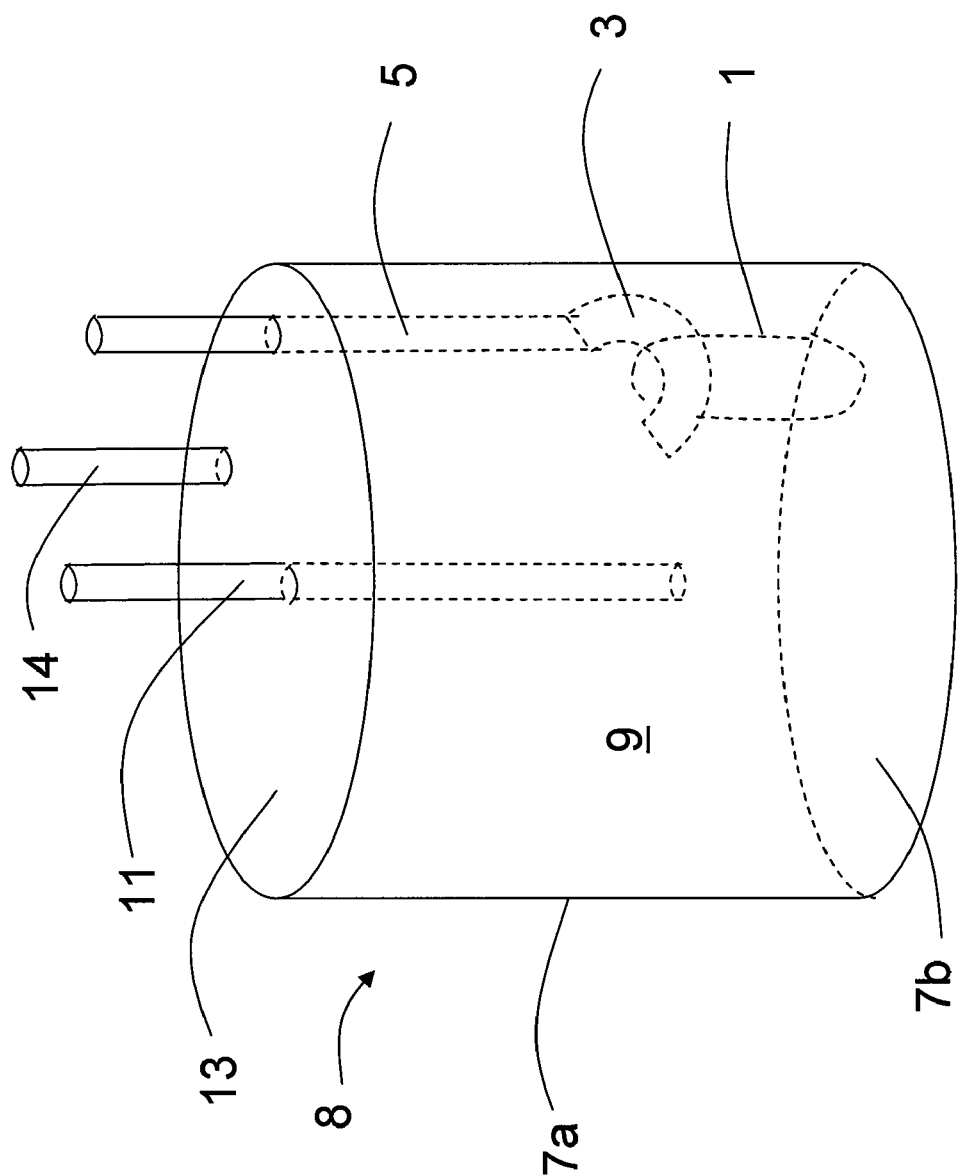
FIG. 1 is a perspective view of the system according to the invention.

One of ordinary skill in the art will recognize that ultrasound energy is sound energy at a frequency above the human hearing range, i.e., above 20 kHz.

One of ordinary skill in the art will recognize that total immersing the medical device in liquid nitrogen will likely achieve a higher degree of kill than partially immersing it given the same set of operating parameters.

Performance of the disclosed method allows a medical device to be sanitized or sterilized. Medical devices to be treated by the method should be resistant to damage at very low temperatures, such as below −196° C. A non-limiting list includes surgical instruments, curettes, dental instruments, medical implants, and dental implants.

A medical device is sterilized or sanitized in the following manner. The surface of the device is at least partially immersed in liquid nitrogen. A sonicating member applies ultrasonic wave energy to the either the liquid nitrogen which in turn transmits the ultrasonic wave energy to the surface. Alternatively, it may impart ultrasonic wave energy directly to the device or indirectly to the device via a device holding member or the vessel and holding member. The holding member is meant to be inclusive of devices that hold or suspend medical devices. The ultrasonic waves create tiny bubbles of gaseous nitrogen on the surface. When these bubbles collapse, significant energy is released. Between the mechanical action of the ultrasound energy and the gaseous nitrogen bubbles bursting and the thermal action of the liquid nitrogen, at least a portion of any microbes present on the surface will tend to be killed. While not bound to any particular theory, we believe that the combined action of the liquid nitrogen and ultrasonic waves destroys the cell walls of the microbes.

The ultrasonic liquid nitrogen treatment is preferably performed under ambient pressure.

In one embodiment, the liquid nitrogen may be subcooled. The advantage of using subcooled liquid nitrogen is that it can receive a significant amount of heat before it starts to boil. When selected, subcooled nitrogen may be maintained at any combination of pressure and temperature in the subcooled region for nitrogen that is achievable using any subcooling technology available at the time it is performed. Preferably, the subcooled nitrogen is at a pressure in the range of 4 bar to 14 bar and at a temperature in the range of −164° C. to −185° C. or −196° C. to −173° C.

Returning to the general description of the disclosed methods and systems, the temperature of the liquid nitrogen in the vessel may be maintained within a desired range by use of mechanical refrigeration or by heat exchange with a suitable low temperature heat exchange fluid such as a lower temperature liquid cryogen, preferably nitrogen.

Suitable sonicating members include a Telsonic Tube Resonator. The sonicating member may be operated at any frequency above sonic. A preferred frequency is greater than 20 kHz to about 150 kHz. Further refinements of this frequency range are greater than 20 kHz to about 50 kHz and from greater than 50 kHz to about 100 kHz. A suitable treatment time depends upon the type of the medical device, type of biological contamination and/or residue, and the amount of contamination or residue. One of ordinary skill in the art will understand that, at a given temperature and pressure, routine experimentation by varying the ultrasound intensity, frequency, and duration may be performed in order to optimize the operating conditions to achieve a desired degree of kill. One of ordinary skill in the art will recognize that there are many known methods for determining the degree of kill.

As best illustrated in FIG. 1, a system includes a securing element 3 depending from a leg element 5. The medical device 1 to be sterilized or sanitized is retained upon the securing element 3. The device 1 may be rigidly secured or loosely held (alternatively, the device may rest upon a bottom 7b of vessel 8). Together, the securing element 3 and leg element 5 comprise a device holding member. The device holding member and device 1 are positioned such that device 1 is immersed within liquid nitrogen 9 in vessel 8. Sonicating member 11 extends at least partially within liquid nitrogen 9. An upper surface of the liquid nitrogen is not depicted, but it is understood that at least a portion of the sonicating member 11 is immersed therein. The vessel 8 includes a bottom 7b from which vertical wall 7a extends.

The system includes a lid 13 having a vent 14 operable into closed or open positions. The lid 13 extends horizontally to upper ends of the vertically extending wall 7a. The lid 13 rests upon a shelf (not depicted) projecting inwardly from an upper end of an inner surface of vertically extending wall 7a. The lid 13 has a lid perimeter sized to conform to a vessel perimeter defined by a horizontal cross-section of the wall 7a above the shelf. The combination of the shelf and perimeter size allows the lid to be securely placed over the vessel 8. The lid 13 has an aperture allowing the sonicating member 11 to extend therethrough and into the liquid nitrogen 9. The vent 14 allows undesirable levels of built-up pressure from vaporization of the liquid nitrogen 9 to be released from the vessel 8.

Figure 2:
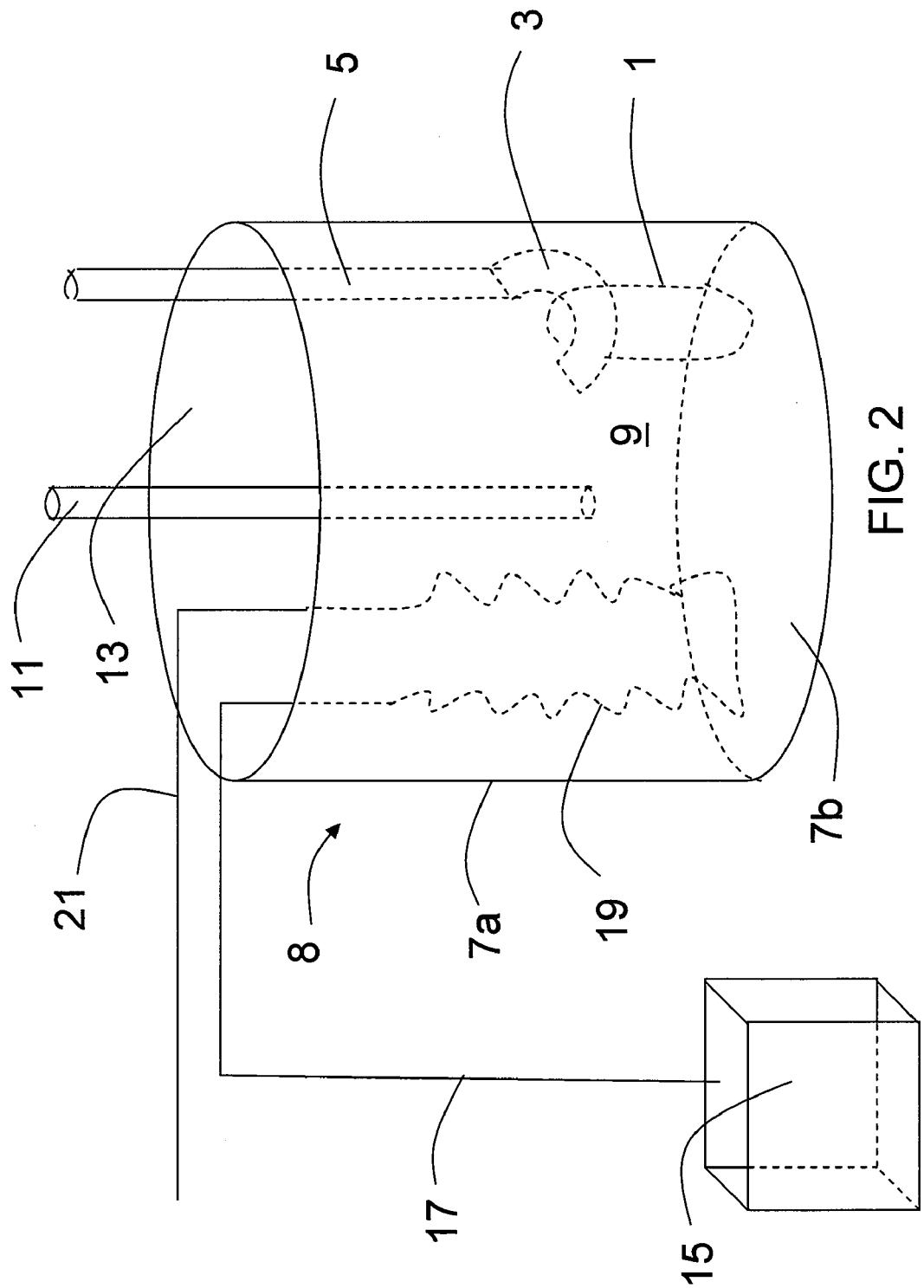
FIG. 2 is a perspective view of an embodiment of the system according to the invention including a cooling member and source of liquid nitrogen.

It should be noted that in each of FIGS. 1 and 2, the wall 7a of the vessel 8 is depicted as transparent in order to more clearly show the inside of vessel 8. It should be noted that the vessel need not be transparent.

While a cylindrically-shaped vessel 8 is depicted, it is understood that the vessel 8 may have any shape that allows containment of the liquid nitrogen 9, a non-limiting example of which includes a cube having the same or different dimensions of length, height, and width. In the case of a cube, it is then understood that such a vessel 8 would have four vertically extending walls. Also, while the securing element 3 is depicted as a semicircle, it is not limited to this shape. Rather, it may have any shape well known to those skilled in the art for holding devices that are to be dipped into a liquid. This includes holding the device, hanging the device, suspending the device, or securing the device, as the device is dipped into a liquid.

The sonicating member 11 need not project upwardly from the vessel 8. Indeed, it may have a height extending to, or below, a top of the vessel 8. It also need not project out from liquid nitrogen 9. Furthermore, it need not extend vertically. Rather, it may extend into the liquid nitrogen 9 horizontally or at an angle. The sonicating member 11 may be built into, suspended from, or supported by, the vertically extending wall 7a, bottom 7b, or any other structure outside the vessel 8.

It is also understood that the edge of the lid 13 need not rest upon a shelf or have a lid perimeter sized to conform to the vessel perimeter. Rather, all or a portion of the lid 13 may extend over or beyond upper ends of the vertically extending wall 7a. Generally speaking, the lid 13 should have a design that prevents vaporization of the liquid nitrogen 9.

As best depicted in FIG. 2, another embodiment of the system according to the invention is also similar to that of FIG. 1, but it also includes a source of liquid nitrogen 15 in fluid communication with a cooling member. The cooling member includes an inlet 17 which receives liquid nitrogen from the source 15 and which is in fluid communication with coil portion 19. The coil portion 19 is in fluid communication with an outlet 21 for venting nitrogen from the system. Alternatively, the outlet 21 is returned to the source 15 where the liquid nitrogen contained therein is chilled and returned to coil portion 19 via inlet 17. The cooling member allows the liquid nitrogen 9 to be maintained in the desired temperature range.

While a cylindrically-shaped vessel 8 is depicted, it is understood that the vessel 8 may have any shape that allows containment of the liquid nitrogen 9, a non-limiting example of which includes a cube having the same or different dimensions of length, height, and width. In the case of a cube, it is then understood that such a vessel 8 would have four vertically extending walls. Also, while the securing element 3 is depicted as a semicircle, it is not limited to this shape. Rather, it may have any shape well known to those skilled in the art for holding devices that are to be dipped into a liquid. This includes holding the device, hanging the device, suspending the device, or securing the device, as the device is dipped into a liquid.

The sonicating member 11 need not project upwardly from the vessel 8. Indeed, it may have a height extending to, or below, a top of the vessel 8. It also need not project out from liquid nitrogen 9. Furthermore, it need not extend vertically. Rather, it may extend into the liquid nitrogen 9 horizontally or at an angle. The sonicating member 11 may be built into, suspended from, or supported by, the vertically extending wall 7a, bottom 7b, or any other structure outside the vessel 8.

Figure 3:
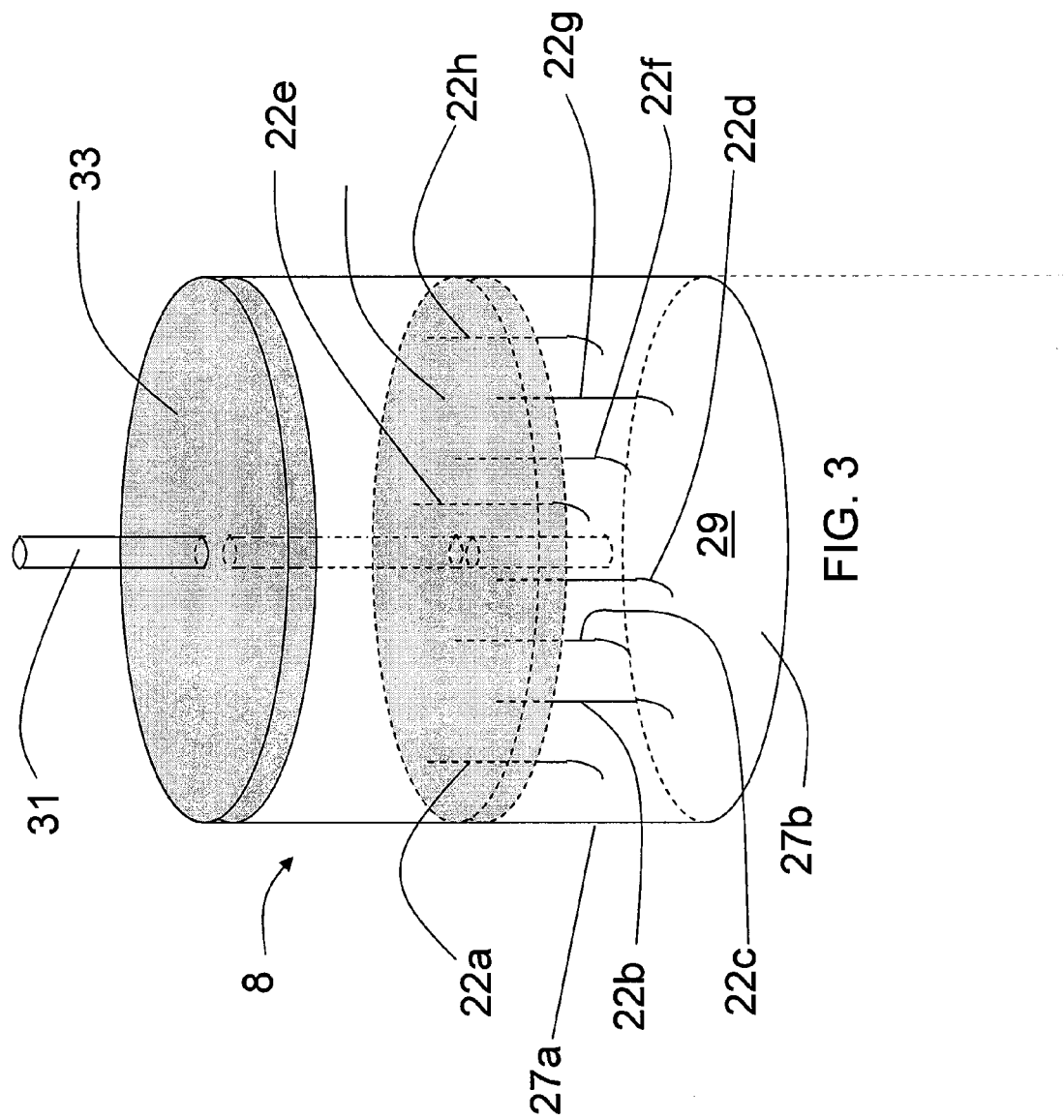
FIG. 3 is a perspective view of an embodiment of the system according to the invention including a variation of the device hanging member.

As best illustrated in FIG. 3, another embodiment of the system according to the invention is also similar to that of FIG. 1, but it includes a variation of the device holding member. It should be noted that wall 27a of the vessel 8 is depicted as transparent in order to more clearly show the inside of vessel 8.

The lid 33 has an aperture allowing the sonicating member 31 to be inserted therethrough. The lid 33 extends horizontally to upper ends of the vertically extending wall 27a. The lid 33 rests upon a shelf (not depicted) projecting inwardly from an upper inner surface of vertically extending wall 27a. The lid 33 also has a lid perimeter sized to conform to a vessel perimeter defined by inner surfaces of a horizontal cross-section of the wall 27a above the shelf. The combination of the shelf and perimeter size allows the lid to be securely placed over the vessel 8. One of ordinary skill in the art will recognize that the shape and size of the various parts of the vessel 8 and the wavelength of the ultrasound energy applied to the device 1 may be designed such that optimal reflection of ultrasound waves from the vessel 8 to the device 1 is achieved thereby maximizing energy density at the surface of the device 1.

In this embodiment, the device holding member includes a horizontally extending element 4 from which hooks 22a-h extend downwardly. The horizontally extending element 4 includes an aperture allowing the sonicating member 31 to be inserted through. Similar to the lid 33, the horizontally extending element 4 has a horizontally extending element perimeter sized to conform to a vessel perimeter defined by inner surfaces of a horizontal cross-section of the wall 27a. Also similar to the lid 33, the horizontally extending element may rest upon a shelf projecting from an inner surface of the wall 27a. The number of hooks 22a-h need not be eight. Rather, the number may be increased to accommodate more devices to be treated or decreased to allow a larger ratio of liquid nitrogen 29 volume per unit device surface area or to accommodate larger-sized devices.

For clarity's sake no devices are depicted as hanging from the hooks 22a-h. Furthermore, while a cylindrically-shaped vessel 8 is depicted, it is understood that the vessel 8 may have any shape allowing containment of the liquid nitrogen 29, a non-limiting example of which includes a cube having the same or different dimensions of length, height, and width. In the case of a cube, it is then understood that such a vessel 8 would have four vertically extending walls. The hooks 22a-h are not limited to the shape depicted. Rather, it may have any shape well known to those skilled in the art for hanging devices to be dipped into a liquid. Finally, the sonicating member 11 need not project upwardly from the vessel 8. Indeed, it may have a height extending to, or below, a top of the vessel 8. It also need not project out from liquid nitrogen 9. Furthermore, it need not extend vertically. Rather, it may extend into the liquid nitrogen 9 horizontally or at an angle. The sonicating member 11 may be built into, suspended from, or supported by, the vertically extending wall 7a, bottom 7b, or any other structure outside the vessel 8.

Figure 4:
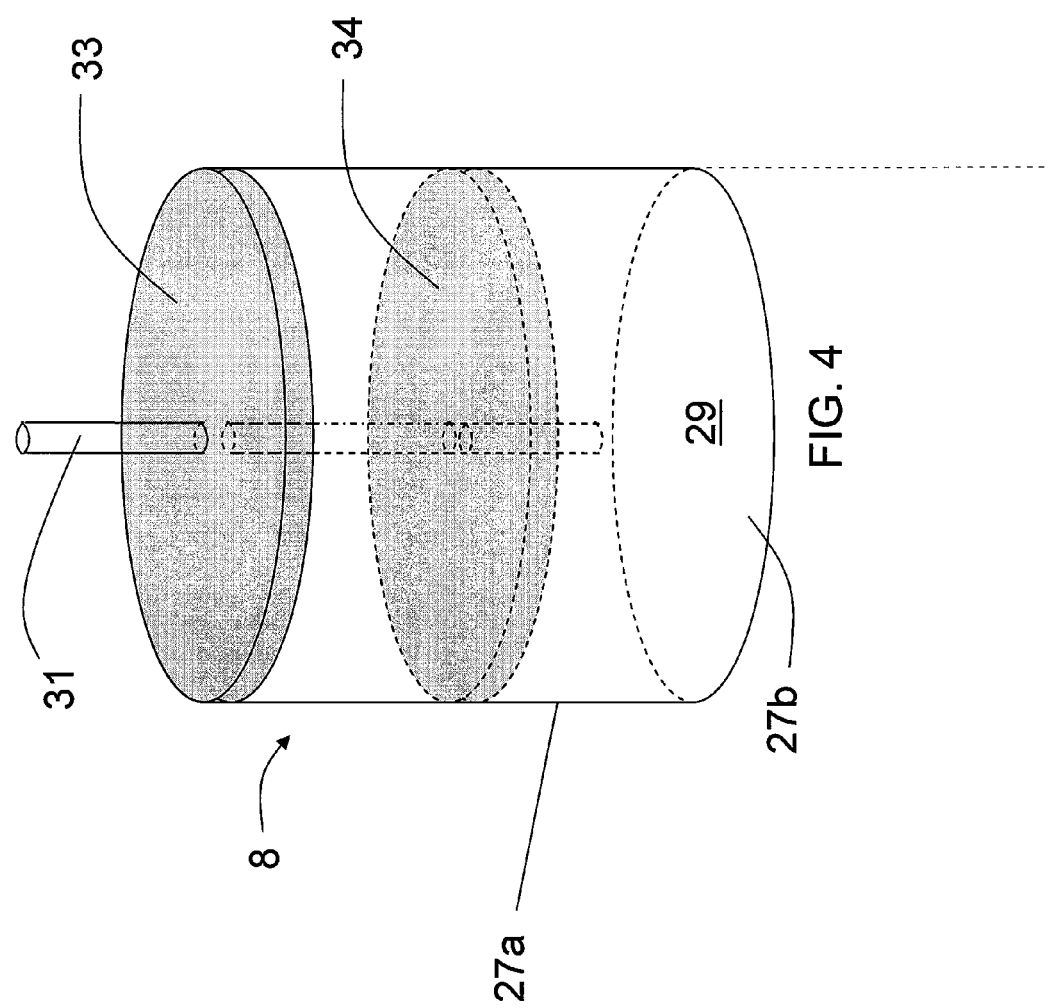
FIG. 4 is a perspective view of an embodiment of the system according to the invention including another variation of the device hanging member.

As best illustrated in FIG. 4, another embodiment of the system according to the invention is also similar to that of FIG. 3, but includes another variation of the device holding member. It should be noted that wall 27a of the vessel 8 is depicted as transparent in order to more clearly show the inside of vessel 8.

The lid 33 has an aperture allowing the sonicating member 31 to be inserted therethrough. The lid 33 extends horizontally to upper ends of the vertically extending wall 27a. The lid 33 rests upon a shelf (not depicted) projecting inwardly from an upper inner surface of vertically extending wall 27a. The lid 33 also has a lid perimeter sized to conform to a vessel perimeter defined by inner surfaces of a horizontal cross-section of the wall 27a above the shelf. The combination of the shelf and perimeter size allows the lid to be securely placed over the vessel 8.

In this embodiment, the device holding member 34 extends horizontally to inner surfaces of the wall 27a while devices (not depicted) rest thereupon. Similar to the lid 33, the device holding member 34 extends to inner surfaces of the wall 27a and has a perimeter sized to conform to a vessel perimeter defined by inner surfaces of a horizontal cross-section of the wall 27a.

The device holding member 34 includes a plurality of apertures, one of which allows the sonicating member 31 to be inserted through. The additional apertures allow the device holding member 34 to allow liquid nitrogen 29 to be circulated therethrough for more uniform sanitization or sterilization of the medical devices. After the high pressure in the vessel 8 is lowered to atmospheric, the apertures further allow the now non-liquid nitrogen to be drained from the device holding member 34 as such member 34 is raised out of the vessel 8.

While a cylindrically-shaped vessel 8 is depicted, it is understood that the vessel 8 may have any shape allowing containment of the liquid nitrogen 29, a non-limiting example of which includes a cube having the same or different dimensions of height, length and width. In the case of a cube, it is then understood that such a vessel 8 would have four vertically extending walls. Also, the sonicating member 11 need not project upwardly from the vessel 8. Indeed, it may have a height extending to, or below, a top of the vessel 8. It also need not project out from liquid nitrogen 9. Furthermore, it need not extend vertically. Rather, it may extend into the liquid nitrogen 9 horizontally or at an angle. The sonicating member 11 may be built into, suspended from, or supported by, the vertically extending wall 7a, bottom 7b, or any other structure outside the vessel 8.

Figure 5:
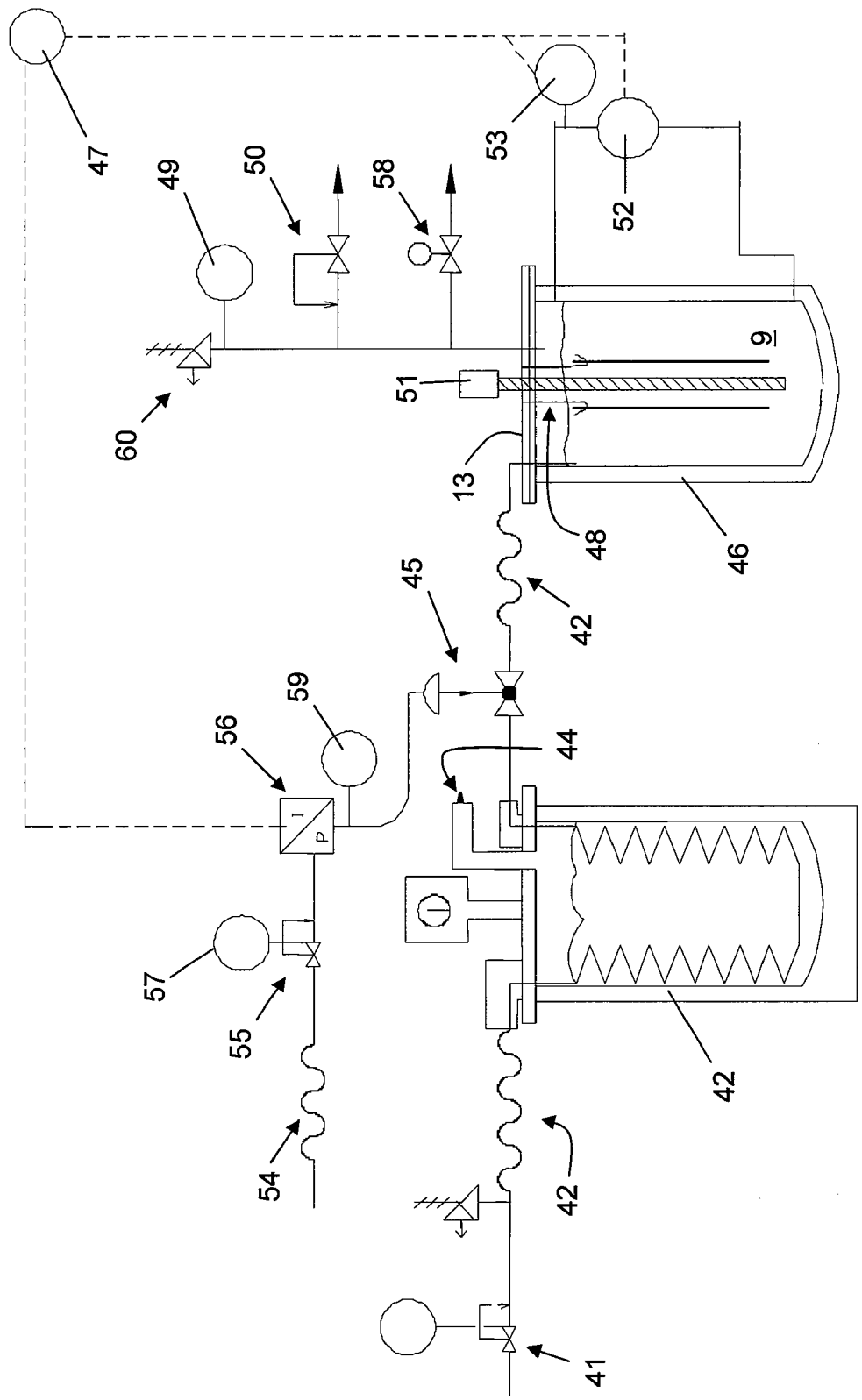
FIG. 5 is a schematic view of an embodiment of the system including a subcooler.

Another embodiment is best shown in FIG. 5. High pressure liquid nitrogen is provided. Typically, it is at a pressure in the range of from 6.8 to 17.2 bar and at a temperature in the range of from −173 to −195° C. Preferably, it is at a pressure in a range of 13-14 bar and at a temperature in range of −184 to −195° C. It flows through pressure regulator 41, tubing 42, and into subcooler 43. The subcooler 43 drops the temperature of the high pressure liquid nitrogen to place it in the subcooled state so any energy put into the system which is transformed into heat will delay boiling of the working fluid. Vent 44 allows overpressure in the subcooler 43 to be released.

The subcooled liquid nitrogen then flows through tubing 42 and into vessel 46. Sonicating member 51 extends into the subcooled liquid nitrogen 9 through lid 13. Devices 1 are held within the subcooled liquid nitrogen 9 with device holding members 48 (alternative, the devices 1 may be secured to a holder, rest upon a tray, or rest upon a bottom surface of vessel 46 or in any other manner disclosed above). Ultrasound energy is imparted to the subcooled liquid nitrogen 9 by sonicating member 51. The ultrasonic waves create tiny bubbles of gaseous nitrogen on the surface of the devices 1. When these bubbles collapse, significant energy is released tending to cause brittle material on the metal surface to detach from the surface. Subcooled liquid nitrogen is maintained in a vacuum insulated vessel 46, advantages of which include noise isolation and reduction of heat leaks from ambient into the subcooled liquid nitrogen. Alternatively, the vessel 46 may utilize foam insulation instead of vacuum insulation. By maintaining the liquid nitrogen in the subcooled condition, addition of heat by the ultrasound energy will not readily result in boiling of the liquid nitrogen.

The level of subcooled liquid nitrogen in vessel 46 is monitored with pressure gauge/transducer 52/53. Based upon the signal from transducer 53, controller 47 sends a signal to the current-to-pressure transducer 56. The transducer 56 controls the pressure of instrument gas flowing through flex hose 54 past instrument gas regulator/pressure gauge 55/57. Pressure gauge 59 is utilized to verify that the instrument gas has been adjusted to the appropriate level by transducer 56. Using this combination of equipment, the sensed liquid level in vessel 46 is used to increase or decrease the flow of high pressure liquid nitrogen in a known manner by way of the control valve 45 that is actuated by instrument air. Alternatively, the control valve 45 may be an electrically actuated valve. In such a case, flex instrument air, hose 54, regulator/pressure gauge 55/57, transducer 56, and gauge 59 are eliminated.

A desired pressure (displayed by pressure gauge 49) within vessel 46 may be maintained by manipulating back pressure regulator 50. Excess gaseous nitrogen may be vented via valve 58. In case the back pressure regulator 50 fails, an over-pressure condition is alleviated by relief valve 60.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A method of disinfecting or sterilizing medical devices, the method comprising the steps of:
providing a vessel containing a fluid consisting essentially of subcooled liquid nitrogen, the liquid nitrogen being supplied to the vessel at a temperature in a range of from about −196° C. to about −173° C. by passing high pressure liquid nitrogen through a subcooler where it is subcooled and allowing the subcooled liquid nitrogen to flow into the vessel;
providing a medical device having microorganisms on a surface thereof;
immersing at least a portion of the surface in the liquid nitrogen within the vessel; and
causing ultrasonic wave energy to be applied to the medical device, wherein the ultrasonic waves have a frequency from greater than 20 kHz to about 150 kHz thereby resulting in the destruction of at least some of the microorganisms.

2. The method of claim 1, wherein the device is a stainless steel surgical instrument.

3. The method of claim 1, wherein the device is a syringe.

4. The method of claim 1, wherein the ultrasonic waves have a frequency of greater than 20 kHz to about 50 kHz.

5. The method of claim 1, wherein the ultrasonic waves have a frequency of about 50 kHz to about 100 kHz.

6. The method of claim 1, wherein a pressure of the liquid nitrogen is in a range of from about 4 bar to about 14 bar.

7. The method of claim 1, wherein the medical device comprises a surgical instrument.

8. The method of claim 1, wherein the medical device comprises a curette.

9. The method of claim 1, wherein the medical device comprises a dental instrument.

10. The method of claim 1, wherein the medical device comprises a medical implant.

11. The method of claim 1, wherein the medical device comprises a dental implant.

12. The method of claim 1, wherein said steps are performed under ambient pressure.

13. The method of claim 1, wherein the medical device is totally immersed within the liquid nitrogen.

14. The method of claim 1, further comprising the step of determining a degree of sanitization or sterilization of the microorganism after said steps of providing, immersing, and causing are performed.

* * * * *